(12) United States Patent
Tondreau et al.

(10) Patent No.: US 8,637,626 B2
(45) Date of Patent: *Jan. 28, 2014

(54) NON-PRECIOUS METAL-CONTAINING 2,8-BIS(IMINO)QUINOLINE COMPLEXES AND THEIR USE AS HYDROSILYLATION CATALYSTS

(75) Inventors: Aaron M. Tondreau, Zurich (CH); Paul J. Chirik, Printon, NJ (US); Johannes G. P. Delis, Bergen op Zoom (NL); Keith J. Weller, Rensselaer, NY (US); Kenrick M. Lewis, Flushing, NY (US); Susan A. Nye, Feura Bush, NY (US)

(73) Assignee: Momentive Performance Materials Inc., Albany, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/302,448

(22) Filed: Nov. 22, 2011

(65) Prior Publication Data

US 2012/0130021 A1    May 24, 2012

Related U.S. Application Data

(60) Provisional application No. 61/417,093, filed on Nov. 24, 2010, provisional application No. 61/417,084, filed on Nov. 24, 2010.

(51) Int. Cl.
*C08G 77/06* (2006.01)

(52) U.S. Cl.
USPC ............. 528/14; 502/150; 502/162; 502/167; 528/21; 528/25; 528/31

(58) Field of Classification Search
None
See application file for complete search history.

(56) References Cited

U.S. PATENT DOCUMENTS

| 3,159,601 A | 12/1964 | Ashby |
| 3,220,972 A | 11/1965 | Lamoreaux |
| 3,775,452 A | 11/1973 | Karstedt |
| 2011/0009565 A1 | 1/2011 | Delis et al. |
| 2011/0009573 A1 | 1/2011 | Delis et al. |

OTHER PUBLICATIONS

"QSAR Model for Ethylene Polymerization Catalyzed by Supported Bis(imino)pyridine Iron Complexes" authored by Cruz et al. and published in Polymer (2007) 48, 7672-7678.*
"Synthesis, Structure, and Catalytic Ethylene Oligomerization of Nickel Complexes Bearing 2-pyrazolyl Substituted 1,10-phenanthroline Ligands" authored by Yang et al. and published in the Journal of Molecular Catalysis A: Chemical (2008) 296, 9-17.*
"A Review of Recent Progress in Catalyzed Homogeneous Hydrosilation" authored by Roy and published in Advances in Organometallic Chemistry (2008) 55, 1-59.*
Speier, J.L., Webster J.A. and Barnes G. H., J. Am. Chem. Soc. 79, 974-979 (1957).
Nesmeyanov, A.N. et al., Tetrahedron 1962, 17, 61-68.
Corey, J.Y. et al., J. Chem. Rev. 1999, 99, 175-292.
C. Randolph, M.S. Wrighton, J. Am. Chem. Soc. 108 (1986) 3366-3374.
Bart et al., J. Am. Chem. Soc., 2004, 126, 13794-13807.
Andrew M. Archer et al., Organometallics, 2006, 25, 4269-4278.
Shu et al., Organometallics, 2010, 29(5), 1168-1173.
Kröll et al., Macromol. Chem. Phys. 2001, 202, No. 5, pp. 645-653.
Glatz et al., Journal of Chromatography A, 1015 (2003) 65-71.
Kim et al., Journal of Organometallic Chemistry 673 (2003) 77-83.
Jie et al., Chinese Journal of Polymer Science vol. 28, No. 3, (2010), 299-304.

* cited by examiner

*Primary Examiner* — Marc Zimmer
(74) *Attorney, Agent, or Firm* — Dominick G. Vicari; Joseph S. Ostroff; Wiggin and Dana LLP

(57) ABSTRACT

Disclosed herein are manganese, iron, cobalt, or nickel complexes containing 2,8-bis(imino)quinoline ligands and their use as catalysts or catalysts precursors for hydrosilylation reactions.

23 Claims, No Drawings

NON-PRECIOUS METAL-CONTAINING 2,8-BIS(IMINO)QUINOLINE COMPLEXES AND THEIR USE AS HYDROSILYLATION CATALYSTS

CROSS-REFERENCE TO RELATED APPLICATION

This application claims priority to U.S. provisional application Nos. 61/417,093 and 61/417,084, both filed Nov. 24, 2010. The disclosures of the application Nos. 61/417,093 and 61/417,084 are herein incorporated by reference in their entireties.

FIELD OF THE INVENTION

This invention relates generally to non-precious metal based complexes, more specifically to manganese, iron, cobalt, or nickel-containing 2,8-bis(imino)quinoline complexes and their use as efficient and selective hydrosilylation catalysts. The invention also relates to non-precious metal based 2,8-bis(imino)quinoline complexes, which themselves are not catalysts, but can be activated in-situ for the hydrosilylation reactions.

BACKGROUND OF THE INVENTION

Hydrosilylation chemistry, typically involving a reaction between a silyl hydride and an unsaturated organic group, is the basis for synthesis routes to produce commercial silicone-based products like silicone surfactants, silicone fluids and silanes as well as many addition cured products like sealants, adhesives, and silicone-based coating products. Conventionally, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's-catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal complex catalysts are widely accepted as catalysts for hydrosilylation reactions, they have several distinct disadvantages. One disadvantage is that the precious metal complex catalysts are inefficient in catalyzing certain reactions. For example, in the case of hydrosilylations of allyl polyethers with silicone hydrides using precious metal complex catalysts, use of an excess amount of allyl polyether, relative to the amount of silicone hydride, is needed to compensate for the lack of efficiency of the catalyst in order to ensure complete conversion of the silicone hydride to a useful product. Moreover, when the hydrosilylation reaction is completed, this excess allyl polyether must either be: (A) removed by an additional step, which is not cost-effective, or (B) left in the product which results in reduced performance of this product in end-use applications. Additionally, the use of an excess amount of allyl polyether typically results in a significant amount of undesired side products such as olefin isomers, which in turn can lead to the formation of undesirably odoriferous byproduct compounds.

Another disadvantage of the precious metal complex catalysts is that they risk not being effective in catalyzing hydrosilylation reactions involving certain type of reaction mixtures. Illustratively, it is known that precious metal complex catalysts are susceptible to catalyst poisons such as phosphorous and amine compounds. Accordingly, for a hydrosilylation involving unsaturated amine compounds, the precious metal catalysts are typically less effective than may be desired in promoting a direct reaction between these unsaturated amine compounds with Si-hydride substrates, and will often lead to the formation of mixtures of undesired isomers.

Further, due to the high price of precious metals, the precious metal-containing catalysts can constitute a significant proportion of the total cost of making silicone formulations. Recently, global demand for precious metals, including platinum, has increased, driving prices for platinum to record highs, creating a need for effective, low cost replacement catalysts.

As an alternative to precious metals, certain iron complexes have been disclosed as suitable for use as hydrosilylation catalysts. Illustratively, technical journal articles have disclosed that $Fe(CO)_5$ catalyzes hydrosilylation reactions at high temperatures. (Nesmeyanov, A. N. et al., Tetrahedron 1962, 17, 61), (Corey, J.Y et al., J. Chem. Rev. 1999, 99, 175), (C. Randolph, M. S. Wrighton, J. Am. Chem. Soc. 108 (1986) 3366). However, unwanted by-products such as the unsaturated silyl olefins, which are resulted from dehydrogenative silylation, were formed as well.

A five-coordinate Fe(II) complex containing a pyridine di-imine (PDI) ligand with isopropyl substitution at the ortho positions of the aniline rings has been used to hydrosilate an unsaturated hydrocarbon (1-hexene) with primary and secondary silanes such as $PhSiH_3$ or $Ph_2SiH_2$ (Bart et al., J. Am. Chem. Soc., 2004, 126, 13794) (Archer, A. M. et al. Organometallics 2006, 25, 4269). However, one of the limitations of these catalysts is that they are only effective with the aforementioned primary and secondary phenyl-substituted silanes reactants, and not with, for example, tertiary or alkyl-substituted silanes such as $Et_3SiH$, or with alkoxy substituted silanes such as $(EtO)_3SiH$.

Recently new and inexpensive Fe, Ni, Co and Mn complexes containing a terdentate nitrogen ligand have been found to selectively catalyze hydrosilylation reactions, as described in co-pending U.S. Patent Application Publication Nos. 20110009573 and 20110009565, the contents of both publications are incorporated herein by reference in their entireties. In addition to their low cost and high selectivity, the advantage of these catalysts is that they can catalyze hydrosilylation reactions at room temperature while precious metal-based catalysts typically work only at elevated temperatures.

Despite these advances, in view of the high demand for silicone-based products, there is a continuing need in the silicones manufacturing community for other non-precious metal-based catalysts that are suitable for catalyzing hydrosilylation reactions.

The preparation and characterization of several iron and cobalt 2,8-bis(imino)quinoline dichloride complexes have been described by Sun et al. in Organometallics, 2010, 29 (5), pp 1168-1173. However, the catalysts disclosed in this reference were described as suitable for use in the context of olefin polymerizations, not in the context of hydrosilylation reactions.

The present invention provides an answer to the need for additional novel non-precious metal-based catalysts that are suitable for catalyzing hydrosilylation reactions.

SUMMARY OF THE INVENTION

In one aspect, the present invention is directed to a compound of Formula (I)

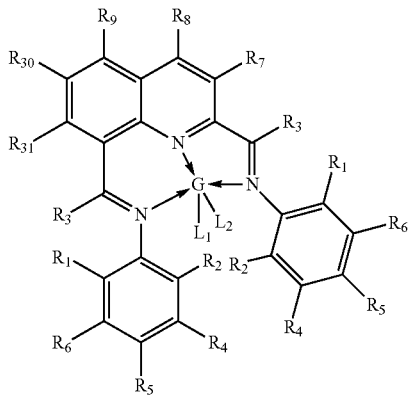

Formula (I)

or Formula (II)

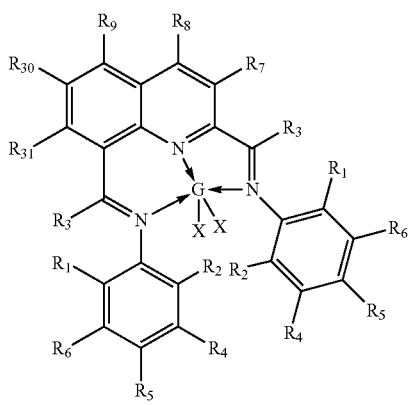

Formula (II)

wherein:

G is Mn, Fe, Ni, or Co;

each occurrence of $R_1$, $R_2$, $R_3$, $R_4$, $R_5$, $R_6$, $R_7$, $R_8$, $R_9$, $R_{30}$ and $R_{31}$ is independently hydrogen, an inert functional group, C1-C18 alkyl, C1-C18 substituted alkyl, aryl, or substituted aryl, wherein optionally each of $R_1$ to $R_9$, $R_{30}$ and $R_{31}$ may independently contain at least one heteroatom;

optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;

$L_1$ and $L_2$ each is a C1-C18 alkyl, C1-C18 substituted alkyl, aryl, substituted aryl, C2-C18 alkene, C2-C18 alkyne, provided that when $L_1$ and $L_2$ are alkene or alkyne, $L_1$ and $L_2$ bond with G through an unsaturated site of alkene or alkyne or $L_1$-$L_2$ together is one of the following:

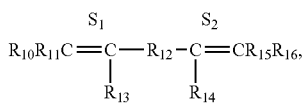

Formula (A)

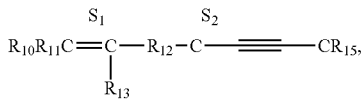

Formula (B)

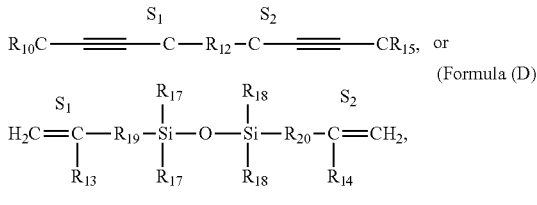

Formula (C)

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;

wherein $L_1$-$L_2$ bonds with G through unsaturated sites $S_1$ and $S_2$; and

X is an anion, preferably $F^-$, $Cl^-$, $Br^-$, $I^-$, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group.

with the proviso that Formula (II) does not encompass the following complexes: [2,8-bis(2,6-dimethyl-$C_6H_3N$=$CCH_3$)$C_9H_5N$]iron dichloride, namely, Iron, dichloro[N,N'-[(2,8-quinolinediyl-κN)diethylidyne]bis[2,6-dimethylbenzenamine-κN]]-; [2,8-bis(2,6-dimethyl-$C_6H_3N$=$CCH_3$)$C_9H_5N$]cobalt dichloride, namely Cobalt, dichloro[N,N'-[(2,8-quinolinediyl-κN)diethylidyne]bis[2,6-dimethylbenzenamine-κN]]-, (SP-5-14)-; [2,8-bis(2,6-dimethyl-4-methyl-$C_6H_2N$=$CCH_3$)$C_9H_5N$]iron dichloride, namely, Iron, dichloro[N,N'-[(2,8-quinolinediyl-κN)diethylidyne]bis[2,4,6-trimethylbenzenamine-κN]]-, and [2,8-bis(2,6-dimethyl-4-methyl-$C_6H_2N$=$CCH_3$)$C_9H_5N$]cobalt dichloride, namely Cobalt, dichloro[N,N'-[(2,8-quinolinediyl-κN)diethylidyne]bis[2,4,6-trimethylbenzenamine-κN]]-.

In another aspect, the present invention is directed to a process for the hydrosilylation of a composition containing a silyl hydride and a compound containing at least one unsaturated group. The process includes: (i) contacting the composition with a metal complex of Formula (I), optionally in the presence of a solvent, to cause the silyl hydride to react with the compound containing at least one unsaturated group to produce a hydrosilylation product containing the metal complex; and (ii) optionally removing the metal complex from the hydrosilylation product.

In yet another aspect, the present invention is directed to an in-situ activation process for the hydrosilylation of a composition containing a silyl hydride and a compound containing at least one unsaturated group. The process includes the steps of: (i) providing a catalyst precursor being a complex having a structural formula according to Formula (II) as described above; (ii) activating the catalyst precursor by contacting the catalyst precursor with an activator in the presence of a liquid medium containing at least one component selected from the group consisting of a solvent, the silyl hydride, the compound containing at least one unsaturated group, and combinations thereof, thereby providing an activated catalyst; (iii) reacting the silyl hydride and the compound containing at least one unsaturated group in the presence of the activated catalyst to produce a hydrosilylation product containing the activated catalyst or derivatives thereof, wherein step (ii) is conducted shortly before, or at the same time as, step (iii); and (iv) optionally removing the activated catalyst or derivatives thereof.

These and other aspects will become apparent upon reading the following detailed description of the invention.

DETAILED DESCRIPTION OF THE INVENTION

In one embodiment of the invention, there is provided a complex of the Formula (I) or Formula (II) as illustrated above. In connection with these formulae, G can be Mn, Fe, Ni, or Co in all the valence states. Advantageously G is iron or cobalt. More advantageously M is Fe, such as Fe (II) and Fe (III).

As used herein, "alkyl" includes straight, branched and cyclic alkyl groups. Specific and non-limiting examples of alkyls include, but are not limited to, methyl, ethyl, propyl, and isobutyl. If not otherwise stated, the alkyl group suitable for the present invention is a C1-C18 alkyl, specifically a C1-C10 alkyl, more specifically, a C1-C6 alkyl.

By "substituted alkyl" herein is meant an alkyl group that contains one or more substituent groups that are inert under the process conditions to which the compound containing these substituent groups is subjected. The substituent groups also do not substantially interfere with the hydrosilylation processes described herein. If not otherwise stated, the substituted alkyl group suitable for the present invention is a C1-C18 substituted alkyl, specifically a C1-C10 substituted alkyl, more specifically a C1-C6 substituted alkyl. In one embodiment, the substituent is an inert functional group as defined herein.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl, and naphthalenyl.

By "substituted aryl" herein is meant an aromatic group that contains one or more substituent groups that are inert under the process conditions to which the compound containing these substituent groups is subjected. The substituent groups also do not substantially interfere with the hydrosilylation processes described herein. Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, the substituents of the substituted aryl groups herein contain 0 to about 30 carbon atoms, specifically, from 0 to 20 carbon atoms, more specifically, from 0 to 10 carbon atoms. In one embodiment, the substituents are the inert functional groups defined herein.

By "alkenyl" herein is meant any straight, branched, or cyclic alkenyl group containing one or more carbon-carbon double bonds, where the point of substitution can be either at a carbon-carbon double bond or elsewhere in the group. Specific and non-limiting examples of alkenyls include, but are not limited to, vinyl, propenyl, allyl, methallyl, and ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds, Advantageously it refers to carbon-carbon double or triple bonds.

By "inert functional group" herein is meant a group other than alkyl, substituted alkyl, aryl or substituted aryl, which is inert under the process conditions to which the compound containing the group is subjected. The inert functional groups also do not substantially interfere with the hydrosilylation processes described herein. Examples of inert functional groups include halo (fluoro, chloro, bromo, and iodo), ether such as $-OR^{30}$ wherein $R^{30}$ is hydrocarbyl or substituted hydrocarbyl. Advantageously, the inert function group is a halo group.

"Heteroatom" herein is meant any of the Group 13-17 elements except carbon, and can include for example oxygen, nitrogen, silicon, sulfur, phosphorus, fluorine, chlorine, bromine, and iodine.

In some embodiments, the complexes disclosed herein include those of Formula (I) and Formula (II) having the following substituents: (1) each occurrence of $R_1$ and $R_2$ is independently hydrogen, or methyl; and/or (2) $R_5$ is hydrogen, methyl, ethyl, n-propyl or isopropyl groups; and/or (3) $R_4$ and $R_6$ are hydrogen; and/or (4) $R_3$ is methyl; and/or (5) $R_7$ to $R_9$, $R_{30}$ and $R_{31}$ are hydrogen.

In connection with Formula (I), in some embodiments, each of $L_1$ and $L_2$ covalently bond to G through a carbon atom. In other embodiments, $L_1$ and $L_2$ do not contain beta hydrogen. Typically, the alpha carbon refers to the carbon that attaches to G. By extension, the beta carbon refers to the carbon that attaches to the alpha carbon. As used herein, beta hydrogen is meant the hydrogen attached to the beta carbon. Advantageously, $L_1$ and $L_2$ are each independently $-CH_2SiR^{60}_3$, wherein each occurrence of $R^{60}$ is C1-C18 alkyl, specifically C1-C10 alkyl, more specifically C1-C6 alkyl, C1-C18 substituted alkyl, specifically C1-C10 substituted alkyl, more specifically C1-C6 substituted alkyl, aryl or substituted aryl. In some embodiments, $R^{60}$ is a methyl or an ethyl group.

Also in connection with Formula (I), in some embodiments, $L_1$ and $L_2$ covalently bond to each other; and $L_1$ and $L_2$ taken together are represented by $L_1$-$L_2$. $L_1$-$L_2$ typically contains at least two unsaturated sites per molecule and is bonded to the metal G through unsaturated sites. Examples of $L_1$-$L_2$ include, but are not limited to, butadienes, 1,5-cyclooctadienes, dicyclopentadienes, norbornadienes, divinyl tetramethyl disiloxane, tretramethyltetravinylcyclotetrasiloxane, and trivinylcyclohexane.

In some embodiments, $L_1$-$L_2$ contains at least four unsaturated sites per molecule. In this circumstance, it is possible to form a metal-2,8-bis(imino)quinoline dimer, (2,8-bis(imino)quinoline-metal-$L_1$-$L_2$-metal-2,8-bis(imino)quinoline), with each metal bonding to two unsaturated sites of $L_1$-$L_2$. Exemplary $L_1$-$L_2$ for the metal-2,8-bis(imino)quinoline dimer is tetravinyltetramethyleyelotetrasiloxane.

In connection with Formula (II), X is an anion such as F⁻, Cl⁻, Br⁻, I⁻, CF₃R⁴⁰SO₃⁻ or R⁵⁰COO⁻, wherein $R^{40}$ is a covalent bond or a C1-C6 alkyl group, and $R^{50}$ is a C1-C10 hydrocarbyl group. Advantageously X is F⁻, Cl⁻, Br⁻, or I⁻. In some embodiments, X is Cl⁻ or Br⁻.

The methods to prepare the compounds represented by structural Formula (II) are known. For example, these compounds can be prepared by reacting a quinoline ligand of Formula (VI) with a metal halide, such as FeCl₂ or FeBr₂, wherein Formula (VI) is represented by

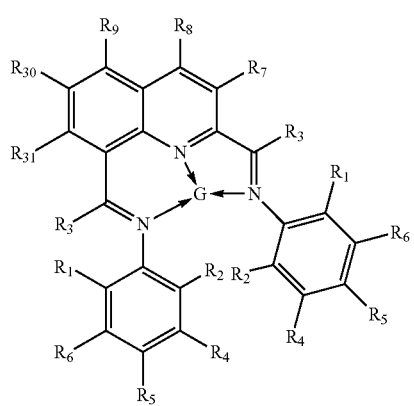

(VI)

wherein

G is Mn, Fe, Ni, or Co;

each occurrence of $R_1$, $R_2$, $R_3$, $R_4$, $R_5$, $R_6$, $R_7$, $R_8$, $R_9$, $R_{30}$ and $R_{31}$ is independently hydrogen, an inert functional group, C1-C18 alkyl, C1-C18 substituted alkyl, aryl, or substituted aryl, wherein optionally each of $R_1$ to $R_9$, $R_{30}$ and $R_{31}$ may independently contain at least one heteroatom;

optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;

Typically, the quinoline ligands of Formula (VI) are produced through condensation of 2,8-diacetylquinoline or its derivatives with an appropriate aniline. An exemplary method to prepare the compound of Formula (II) is described by Zhang et al. in Organometallics, 2010, 29 (5), pp 1168-1173, the disclosure of which is incorporated herein by reference in its entirety.

When $L_1$ and $L_2$ are C1-C18 alkyl, C1-C18 substituted alkyl, aryl, substituted aryl, the compound of Formula (I) can be prepared by reacting a complex of Formula (II) with $L_1$, $L_2$ containing alkylating agents selected from the group consisting of alkali metal salts, alkaline earth metal salts, Grignards, aluminum alkyls, mercury alkyls, thallium alkyls.

As used herein, alkali metal salts include for example monoalkyl salts of lithium, sodium, potassium, rubidium and cesium. Alkaline earth metal salts include for example dialkyl salts of beryllium, magnesium, calcium, strontium and barium. Grignards suitable for the present invention include alkyl magnesium halides. Aluminum alkyls include for example trialkyl aluminum salts. Mercury alkyls refer to dialkyl mercury salts. Thallium alkyls include monoalkyl and trialkyl thallium salts.

When $L_1$ and $L_2$ are C2-C18 alkene or C2-C18 alkyne the compound of formula (I) can be prepared by reacting the compound of Formula (II) with $L_1$ and $L_2$. When $L_1$ and $L_2$ taken together are $L_1$-$L_2$ as defined above in connection with Formula (I), the compound of formula (I) can be prepared by reacting the compound of Formula (II) with $L_1$-$L_2$.

The metal complexes of Formula (I) and Formula (II) are useful for catalyzing industrially practiced hydrosilylation reactions. For example, (1) the crosslinking of silicone hydride fluids with terminally unsaturated polymers, and (2) hydrosilylation of terminally unsaturated amines with tertiary silanes. Accordingly, the metal complexes of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

When used as catalysts or catalyst precursors for the hydrosilylation reactions, the complexes of Formula (I) and Formula (II) can be unsupported or immobilized on a support material, for example, carbon, silica, alumina, MgCl₂ or zirconia, or on a polymer or prepolymer, for example polyethylene, polypropylene, polystyrene, or poly(aminostyrene). The metal complexes can also be supported on dendrimers.

In some embodiments, for the purposes of attaching the metal complexes of the invention to a support, it is desirable that at least one of $R_7$, $R_8$, $R_9$, $R_{30}$ and $R_{31}$ of the metal complexes of Formulae (I) and (II) has a functional group that is effective to covalently bond to the support. Exemplary functional groups include but are not limited to SH, COOH, NH₂ or OH groups.

In certain embodiments, silica supported catalysts or catalyst precursors may be prepared via Ring-Opening Metathesis Polymerization (ROMP) technology as discussed in the literature, for example Macromol. Chem. Phys. 2001, 202, No. 5, pages 645-653, Journal of Chromatography A, 1025 (2003) 65-71, the content of which is incorporated herein by reference in its entirety.

Another way to immobilize catalysts or catalyst precursors on the surface of dendrimers is by the reaction of Si—Cl bonded parent dendrimers and functionalized metal complexes of Formula (I) or (II) in the presence of a base as illustrated by Kim et al. in Journal of Organometallic Chemistry 673 (2003) 77-83, the content of which is incorporated herein by reference in its entirety.

The complexes of Formula (I) can be used directly as catalysts for the hydrosilylation of a composition containing a silyl hydride and a compound having at least one unsaturated group. The process includes contacting the composition with a metal complex of Formula (I), either supported or unsupported, to cause the silyl hydride to react with the compound having at least one unsaturated group to produce a hydrosilylation product containing the metal complex catalyst. The hydrosilylation reaction can be conducted optionally in the presence of a solvent. If desired, when the hydrosilylation reaction is completed, the metal complex can be removed from the hydrosilylation product by magnetic separation, filtration, and/or other technologies known to a person skilled in the art.

Alternatively, the catalyst precursors of the invention, namely, the complexes of Formula (II) can be activated in-situ to generate reactive catalysts for the hydrosilylation of a composition containing a silyl hydride and a compound having at least one unsaturated group. The process includes the steps of: (i) providing a catalyst precursor being a complex having a structural formula according to Formula (II); (ii) activating the catalyst precursor by contacting the catalyst precursor with an activator in the presence of a liquid medium containing at least one component selected from the group consisting of a solvent, the silyl hydride, the compound containing at least one unsaturated group, and combinations thereof, thereby providing an activated catalyst; (iii) reacting the silyl hydride and the compound containing at least one unsaturated group in the presence of the activated catalyst to produce a hydrosilylation product containing the activated catalyst or derivatives thereof, wherein step (ii) is conducted shortly before, or at the same time as, step (iii); and (iv) optionally removing the activated catalyst or derivatives thereof.

As used herein, it is appreciated that "in-situ" means that (1) the catalyst precursor is activated while the catalyst precursor is present in the reaction mixture of the silyl hydride and the unsaturated substrate, or (2) the catalyst precursor is partially or fully activated before the partially or fully activated catalyst is present in the reaction mixture of the silyl hydride and the unsaturated substrate. It is intended to include the following situations: (a) contacting the catalyst precursor with an activator in the presence of a solvent to provide an admixture shortly before contacting the admixture with the silyl hydride and the unsaturated substrate, or (b) contacting the catalyst precursor with an activator in the presence of the silyl hydride to provide an admixture shortly before contacting the admixture with the unsaturated substrate, and if necessary, the remaining amount of the silyl hydride, or (c) contacting the catalyst precursor with an activator in the presence of the unsaturated substrate to provide an admixture shortly before contacting the admixture with the silyl hydride, and if necessary, the remaining amount of the unsaturated substrate, or (d) contacting the catalyst precursor with an activator at the same time as, or after, contacting the catalyst precursor with the silyl hydride and the unsaturated substrate.

By "shortly before", it is meant a time period of less than 24 hours, preferably less than 2 hours, more preferably, less than 30 minutes depending upon the properties of the particular catalyst precursor and the activator used.

The activators suitable for the present invention include reducing agents having a reduction potential more negative than −0.6 v versus ferrocene in the presence of nitrogen, as described in *Chem. Rev.* 1996, 96, 877-910. In one embodiment, the reducing agents have a reduction potential in the range of −2.8 to −3.1 v versus ferrocene. Exemplary reducing agents include, but are not limited to, sodium naphthalenide, Mg(butadiene).2THF, NaEt$_3$BH, LiEt$_3$BH, Mg(Anthracenide).3THF, diisobutylaluminium hydride, and combinations thereof. In some embodiments, the reducing agent is Mg(butadiene).2THF or NaEt$_3$BH.

In connection with the use of complexes of Formulae (I) and (II) in the hydrosilylation reaction, when the silyl hydride is $Q_uT_vT_p^HD_wD^H_xM^H_yM_z$, the compound containing an unsaturated group is an alkyne, a C2-C18 olefin, advantageously alpha olefins, an unsaturated aryl ether, a vinyl-functional silane, and combinations thereof.

As used herein, an "M" group represents a monofunctional group of formula R'$_3$SiO$_{1/2}$, a "D" group represents a difunctional group of formula R'$_2$SiO$_{2/2}$, a "T" group represents a trifunctional group of formula R'SiO$_{3/2}$, and a "Q" group represents a tetrafunctional group of formula SiO$_{4/2}$, an "M$^H$" group represents H$_g$R'$_{3-g}$SiO$_{1/2}$, a "T$^H$" group represents HSiO$_{3/2}$, and a "D$^H$" group represents R'HSiO$_{2/2}$, where each occurrence of R' is independently C1-C18 alkyl, C1-C18 substituted alkyl, wherein R' optionally contains at least one heteroatom. As used herein, g has a value of from 0 to 3, each of p, u, v, y and z is independently from 0 to 20, w and x are independently from 0 to 1000, provided that p+x+y equals 1 to 3000, and the valences of the all the elements in the silyl hydride are satisfied. Advantageously, p, u, v, y, and z are from 0 to 10, w and x are from 0 to 100; wherein p+x+y equals 1 to 100.

In some embodiments, the silyl hydride has a structure of

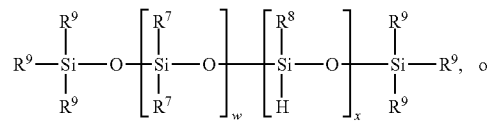
(Formula VII)

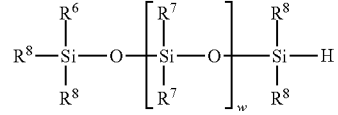
(Formula VIII)

wherein each occurrence of R$^7$, R$^8$ and R$^9$ is independently a C1-C18 alkyl, C1-C18 substituted alkyl, aryl, or a substituted aryl, R$^6$ is a C1-C18 alkyl, C1-C18 substituted alkyl, aryl, or a substituted aryl, and w and x are independently greater than or equal to 0.

When the silyl hydride is selected from the group consisting of R$_a$SiH$_{4-a}$, (RO)$_a$SiH$_{4-a}$, HSiR$_a$(OR)$_{3-a}$, and combinations thereof, wherein each occurrence of R is independently C1-C18 alkyl, C1-C18 substituted alkyl, aryl or substituted aryl, wherein R optionally contains at least one heteroatom, a has a value of from 1 to 3, the compound containing an unsaturated group is selected from the group consisting of a unsaturated polyether such as an alkyl-capped allyl polyether, a vinyl functionalized alkyl-capped allyl or methallyl polyether, an alkyne, an unsaturated cycloalkyl epoxide, a terminally unsaturated acrylate or methyl acrylate, an unsaturated aryl ether, an unsaturated aromatic hydrocarbon, an unsaturated cycloalkane, a vinyl-functionalized polymer, a vinyl-functionalized silane, a vinyl-functionalized silicone, and combinations thereof.

Unsaturated polyethers suitable for the hydrosilylation reaction preferably are polyoxyalkylenes having the general formula:

R$^1$(OCH$_2$CH$_2$)$_z$(OCH$_2$CHR$^3$)$_w$-OR$^2$     Formula (III)

or

R$^2$O(CHR$^3$CH$_2$O)$_w$(CH$_2$CH$_2$O)$_z$-CR$^4$$_2$—C≡C—CR$^4$$_2$—(OCH$_2$CH$_2$)$_z$(OCH$_2$CHR$^3$)$_w$R$^5$     Formula (IV)

or

H$_2$C=CR$^4$CH$_2$O(CH$_2$OCH$_2$)$_z$(CH$_2$O CHR$^3$)$_w$CH$_2$CR$^4$=CH$_2$     Formula (V)

wherein R$^1$ denotes an unsaturated organic group containing from 2 to 10 carbon atoms such as allyl, methallyl propargyl or 3-pentynyl. When the unsaturation is olefinic, it is desirably terminal to facilitate smooth hydrosilylation. However, when the unsaturation is a triple bond, it may be internal. R$^2$ is vinyl, or a polyether capping group of from 1 to 8 carbon atoms such as the alkyl groups: CH$_3$, n-C$_4$H$_9$, t-C$_4$H$_9$ or i-C$_8$H$_{17}$, the acyl groups such as CH$_3$COO, t-C$_4$H$_9$COO, the beta-ketoester group such as CH$_3$C(O)CH$_2$C(O)O, or a trialkylsilyl group. R$^3$ and R$^4$ are independently monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. R$^4$ may also be hydrogen. R$^3$ and R$^4$ are most preferably methyl. R$^5$ is hydrogen, vinyl or a polyether capping group of from 1 to 8 carbon atoms as defined herein above for $R^2$. Each occurrence of z is 0 to 100 inclusive and each occurrence of w is 0 to 100 inclusive. Preferred values of z and w are 1 to 50 inclusive.

Vinyl functionalized silicones are $Q_u T_v T_p^{vi} D_w D^{vi}{}_x M^{vi}{}_y M_z$ (Formula IX), wherein Q is $SiO_{4/2}$, T is R' $SiO_{3/2}$, $T^{vi}$ is $R^{12}SiO_{3/2}$, D is $R'_2SiO_{2/2}$, $D^{vi}$ is R' $R^{12}SiO_{2/2}$, $M^{vi}$ is $R^{12}{}_g R'_{3-g}SiO_{1/2}$, M is $R'_3SiO_{1/2}$; $R^{12}$ is vinyl; each occurrence of R' is independently C1-C18 alkyl, C1-C18 substituted alkyl, aryl, substituted aryl, wherein R' optionally contain at least one heteroatom; each g has a value of from 1 to 3, p is from 0 to 20, u is from 0 to 20, v is from 0 to 20, w is from 0 to 5000, x is from 0 to 5000, y is from 0 to 20, and z is from 0 to 20, provided that v+p+w+x+y equals 1 to 10,000, and the valences of all of the elements in the compound containing at least one unsaturated group are satisfied.

In some embodiments, suitable vinyl functionalized silicones are represented by Formula (X):

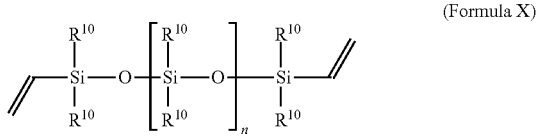

(Formula X)

wherein each occurrence of $R^{10}$ is independently a C1-C18 alkyl, C1-C18 substituted alkyl, vinyl, aryl, or a substituted aryl, n is greater than or equal to zero.

Vinyl functional silanes are $R^{14}{}_a SiR^{15}{}_{4-a}$, wherein $R^{14}$ is C1-C18 alkyl, C1-C18 substituted alkyl, aryl, substituted aryl, wherein $R^{14}$ optionally contains at least one heteroatom, and $R^{15}$ is vinyl, where a is 0 to 3.

Alkenes suitable for the hydrosilylation reaction are not particularly limited. Advantageously, suitable olefins are C2-C18 alpha olefins such as 1-octene. Exemplary terminally unsaturated amines include allyl amine, N,N-dimethylallylamine. Exemplary unsaturated cycloalkyl epoxides include limonene oxides, and vinyl cyclohexyl epoxides such as 4-vinyl-1-cyclohexene 1,2-epoxide. Exemplary unsaturated alkyl epoxides include 1,2-epoxy-7-octene, 1,2-epoxy-9-decene, butadiene monoxide, 2-methyl-2-vinyloxirane, 1,2-epoxy-5-hexene, and allyl glycidyl ether. Exemplary unsaturated aromatic hydrocarbons include styrene. Exemplary unsaturated cycloalkanes include trivinyl cyclohexane. Exemplary unsaturated polymers include terminally unsaturated polyurethane polymers.

Solvents suitable for the hydrosilylation reaction of the invention include, but are not limited to non-polar, aliphatic and aromatic hydrocarbon solvents. The temperature range for the process of the hydrosilylation is from −50° C. to 250° C., advantageously from −10 to 150° C. The silyl hydride and the compound having at least one unsaturated group are typically mixed in a molar ratio ranging from about 0.5:2 to about 1:0.8, advantageously from about 0.8:1.3 to about 1:0.9, and more advantageously in a molar ratio of 1:1 of the reactive groups. For the in-situ activation process, the molar ratio of the reducing agent or the activator with respect to the catalyst precursor is between about 5:1 and 0.8:1, advantageously between about 2:1 and 0.8:1, more advantageously between about 1.2:1 to about 0.8:1. The amount of catalyst in the reaction mixture calculated on ppm level of the metal in the total mass of the mixture is 1-10,000 ppm, advantageously 10-5000 ppm, more advantageously 20-2000 ppm. For an in-situ activation, a nitrogen atmosphere is preferred, but is not absolutely necessary.

The metal complexes of Formula (I) and the activated metal complexes of Formula (II) of the invention are efficient and selective in catalyzing hydrosilylation reactions. For example, when the metal complexes of the invention are employed in the hydrosilylation of an alkyl-capped allyl polyether and a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is unsaturated amine compound, the hydrosilylation product is essentially free of internal addition products and isomerization products of the unsaturated amine compound. As used herein, "essentially free" is meant no more than 10 wt %, preferably 5 wt % based on the total weight of the hydrosilylation product. "Essentially free of internal addition products" is meant that silicon is added to the terminal carbon.

The metal complexes of the invention can also be used in a process for preparing a silylated polyurethane, which includes the step of contacting terminally unsaturated polyurethane polymer with a silyl hydride in the presence of a complex of Formula (I), or activated complex of Formula (II).

The following examples are intended to illustrate, but in no way limit the scope of the present invention. All parts and percentages are by weight and all temperatures are in degrees Celsius unless explicitly stated otherwise.

EXAMPLES

General Considerations:

All air- and moisture-sensitive manipulations were carried out using standard vacuum line, Schlenk, and cannula techniques or in an MBraun inert atmosphere drybox containing an atmosphere of purified nitrogen. Solvents for air- and moisture-sensitive manipulations were initially dried and deoxygenated using literature procedures. See for example Pangborn et al., J. Organometallics 1996, 15, 1518.

EXAMPLE 1

Hydrosilylation of 1-Octene with Methylbis(trimethylsilyloxy)silane ($MD^HM$) using Mg(butadiene) .2THF as an activator and ($^{2,6-Me2}$Quinoline)$FeCl_2$ as a Catalyst Precursor Catalyst precursor, [2,8-bis(2,6-dimethyl-$C_6H_3N$=$CCH_3$)$C_9H_5N$]iron dichloride, hereafter($^{2,6-Me2}$Quinoline)$FeCl_2$, which structure is shown below, was synthesized according to: Zhang, S.; Sun, W.; Xiao, T.; Hao, X. Organometallics (2010), 29 (5), 1168-1173.

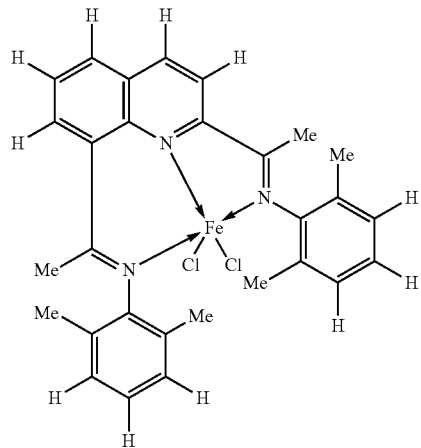

In an inert atmosphere, to a scintillation vial with stir bar was added 0.100 g (0.89 mmol) of 1-octene and 0.192 g (0.86 mmol, 0.97 eq to olefin) of MD$^H$M, followed by 0.004 g (0.01 mmol) of ($^{2,6\text{-}Me2}$Quinoline)FeCl$_2$ (1 mol % to silane), and 0.003 g (0.015 mmol) of Mg(butadiene).2THF. The reaction was stirred for one hour, quenched in air and analyzed by Gas Chromatography (GC) and NMR, showing 70% conversion to the desired hydrosilylation product. Only the desired anti-Markovnikov addition product and unreacted starting materials were observed. No evidence was seen for any isomerization of the 1-octene or any hydrosilylation products derived therefrom.

EXAMPLE 2

Hydrosilylation of 1-Octene with Methylbis(trimethylsilyloxy)silane (MD$^H$M) using NaEt$_3$BH as an activator and ($^{2,6\text{-}Me}$Quinoline)FeBr$_2$ as a Catalyst Precursor Catalyst precursor, [2,8-bis(2,6-dimethyl-C$_6$H$_3$N=CCH$_3$)C$_9$H$_5$N]iron dibromide, hereafter ($^{2,6\text{-}Me2}$Quin-oline)FeBr$_2$, was prepared as follows: A scintillation vial was charged with 0.150 g (0.357 mmol) of 2,8-bis(1-aryliminoethyl)quinoline and 0.077 g (0.357 mmol) of iron dibromide, followed by the addition of 10 mL of THF. The reaction was stirred overnight, at which time the volume of THF was reduced to about 5 mL. Then 10 mL of pentane was added, inducing precipitation of the product. The green powder was collected on a frit and dried under reduced pressure, yielding 0.210 g (92%) of ($^{2,6\text{-}Me2}$Quinoline)FeBr$_2$.

Hydrosilylation: A procedure similar to that in Example 1 was used, but with 0.100 g (0.89 mmol) of 1-octene and 0.192 g (0.86 mmol, 0.97 eq to olefin) of MD$^H$M, followed by 0.010 g (0.02 mmol) $^{of}$ ($^{2,6\text{-}Me2}$Quinoline)FeBr$_2$ (2 mol % to silane), and 0.040 mL (0.04 mmol) of 1M NaEt$_3$BH in toluene. The reaction was stirred for one hour, quenched in air and analyzed by GC, showing 70% conversion to the desired hydrosilylation product. Only the desired anti-Markovnikov addition product and unreacted starting materials were observed. No evidence was seen for any isomerization of the 1-octene or any hydrosilylation products derived therefrom.

EXAMPLE 3

Hydrosilylation of 1-Octene with Methylbis(trimethylsilyloxy)silane (MD$^H$M) using Mg(butadiene).2THF as an activator and ($^{2,6\text{-}Me2}$Quinoline)FeBr$_2$ as a Catalyst Precursor A procedure similar to that in Example 1 was used, but with 0.100 g (0.89 mmol) of 1-octene and 0.192 g (0.86 mmol, 0.97 eq to olefin) of MD$^H$M, followed by 0.010 g (0.02 mmol) of ($^{2,6\text{-}Me2}$Quinoline)FeBr$_2$ (2 mol % to silane) and 0.007 g (0.03 mmol) of Mg(butadiene).2THF. The reaction was stirred for one hour at room temperature (23° C.), quenched in air and analyzed by GC, showing 50% conversion to the desired hydrosilylation product. Only the desired anti-Markovnikov addition product and unreacted starting materials were observed. No evidence was seen for any isomerization of the 1-octene or any hydrosilylation products derived therefrom.

EXAMPLE 4

Preparation of ($^{2,6\text{-}Me2}$Quinoline)Fe(CH$_2$SiMe$_3$)$_2$

To a round bottomed flask charged with 0.075 g (0.12 mmol) of ($^{2,6\text{-}Me2}$Quinoline)FeBr$_2$ was added approximately 10 mL of diethyl ether. The flask was chilled to −35° C. and a solution containing 0.023 g (0.24 mmol) of LiCH$_2$SiMe$_3$ and approximately 10 mL of diethyl ether was added. The slurry was stirred and allowed to warm to ambient temperature. After stirring for one hour, the reaction mixture was filtered through Celite® and the volatiles were removed in vacuo. The resulting burgundy solid was washed with approximately 5 mL of cold pentane yielding 0.060 g (73%) of ($^{2,6\text{-}Me2}$Quinoline)Fe(CH$_2$SiMe$_3$)$_2$. $^1$NMR δ=294.41, 112.07, 58.47, 48.61, 32.19, 10.19, −8.85, −10.02, −10.56, −11.06, −12.19, −18.13, −20.54, −29.84, −36.02, −44.48, −159.63. The structure of ($^{2,6\text{-}Me2}$Quinoline)Fe(CH$_2$SiMe$_3$)$_2$ is represented by Formula (I) wherein R$_1$, R$_2$, R$_3$ are —CH$_3$, R$_4$, R$_5$, R$_6$, R$_7$, R$_8$, R$_9$, R$_{30}$, and R$_{31}$ are H, and both L$_1$ and L$_2$ are —CH$_2$Si(CH$_3$)$_3$.

EXAMPLE 5

Hydrosilylation of 1-Octene with Methylbis(trimethylsilyloxy)silane (MD$^H$M) using ($^{2,6\text{-}Me2}$Quinoline)Fe(CH$_2$SiMe$_3$)$_2$ In an inert atmosphere, to a scintillation vial with stir bar was added 0.100 g (0.89 mmol) of 1-octene and 0.192 g (0.86 mmol, 0.97 eq to olefin) of MD$^H$M, followed by 0.010 g (0.02 mmol) of ($^{2,6\text{-}Me}$Quinoline)Fe(CH$_2$SiMe$_3$)$_2$. The reaction was stirred for one hour at 60° C., quenched in air and analyzed by GC, showing 40% conversion to the desired hydrosilylation product. No evidence was seen for any isomerization of the 1-octene or any hydrosilylation products derived there from.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:
1. A complex of Formula (I)

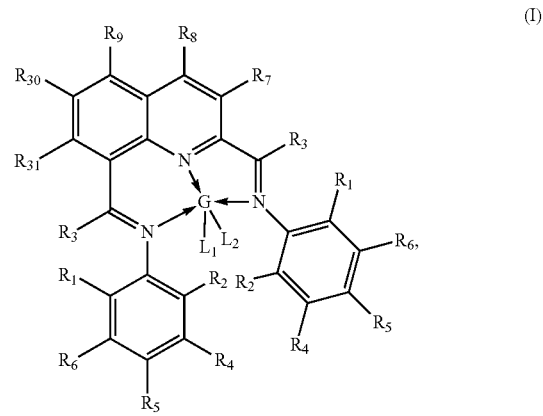

wherein:
G is Mn, Fe, Ni, or Co;
each occurrence of R$_1$, R$_2$, R$_3$, R$_4$, R$_5$, R$_6$, R$_7$, R$_8$, R$_9$, R$_{30}$ and R$_{31}$ is independently hydrogen, C1-C18 alkyl, C1-C18 substituted alkyl, aryl, or substituted aryl, wherein optionally each of R$_1$ to R$_9$, R$_{30}$ and R$_{31}$ may independently contain at least one heteroatom;

optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;

$L_1$ and $L_2$ each is a C1-C18 alkyl, C1-C18 substituted alkyl, aryl, substituted aryl, C2-C18 alkenyl or C2-C18 alkynyl, or $L_1$-$L_2$ together is one of the following:

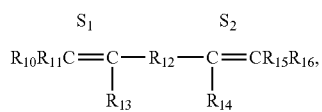

Formula (A)

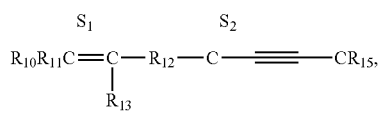

Formula (B)

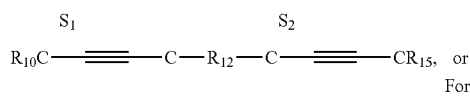

Formula (C)

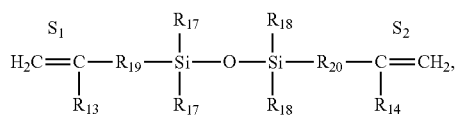

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;

wherein $L_1$-$L_2$ bonds with G through unsaturated sites $S_1$ and $S_2$.

2. A complex according to Formula (I) of claim 1 wherein each occurrence of $R_1$ and $R_2$ is independently hydrogen or a methyl group.

3. A complex according to Formula (I) of claim 1 wherein $R_5$ is hydrogen, a methyl, ethyl, n-propyl or isopropyl group.

4. A complex according to Formula (I) of claim 1 wherein $R_3$ is methyl.

5. A complex according to Formula (I) of claim 1 wherein $R_4$ and $R_6$ are hydrogen.

6. A complex according to Formula (I) of claim 1 wherein $R_7$ to $R_9$, $R_{30}$ and $R_{31}$ are hydrogen.

7. A complex according to Formula (I) of claim 1 wherein each of $L_1$ and $L_2$ is independently —$CH_2SiR^{60}_3$, each occurrence of $R^{60}$ is C1-C18 alkyl, C1-C18 substituted alkyl, aryl or substituted aryl.

8. A complex according to Formula (I) of claim 1 wherein $L_1$-$L_2$ is selected from the group consisting of butadienes, 1,5-cyclooctadienes, dicyclopentadienes, norbornadienes, trivinylcyclohexane, tetramethyltetravinylcyclotetrasiloxane, and divinyl tetramethyl disiloxane.

9. A complex according to Formula (I) of claim 1 wherein G is Fe.

10. A complex according to Formula (I) of claim 1 wherein the complex is immobilized on a support.

11. The complex of claim 10 wherein the support is selected from the group consisting of carbon, silica, alumina, $MgCl_2$, zirconia, polyethylene, polypropylene, polystyrene, poly(aminostyrene), dendrimers, and combinations thereof.

12. The complex of claim 10 wherein at least one of $R_7$, $R_8$, $R_9$, $R_{30}$ and $R_{31}$ contains a functional group that covalently bonds with the support.

13. A process for the hydrosilylation of a composition containing a silyl hydride and a compound containing at least one unsaturated group, the process comprising: (i) contacting the composition with a complex according to Formula (I), optionally in the presence of a solvent, to cause the silyl hydride to react with the compound containing at least one unsaturated group to produce a hydrosilylation product containing said complex, and (ii) optionally removing the complex from the hydrosilylation product, wherein the complex of Formula (I) is

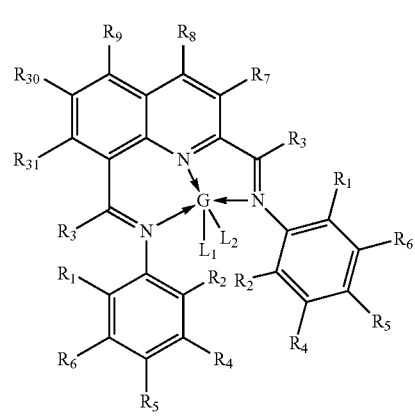

(I)

wherein:

G is Mn, Fe, Ni, or Co;

each occurrence of $R_1$, $R_2$, $R_3$, $R_4$, $R_5$, $R_6$, $R_7$, $R_8$, $R_9$, $R_{30}$ and $R_{31}$ is independently hydrogen, an inert functional group, C1-C18 alkyl, C1-C18 substituted alkyl, aryl, or substituted aryl, wherein optionally each of $R_1$ to $R_9$, $R_{30}$ and $R_{31}$ may independently contain at least one heteroatom;

optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;

$L_1$ and $L_2$ each is a C1-C18 alkyl, C1-C18 substituted alkyl, aryl, substituted aryl, C2-C18 alkenyl or C2-C18 alkynyl, or $L_1$-$L_2$ together is one of the following:

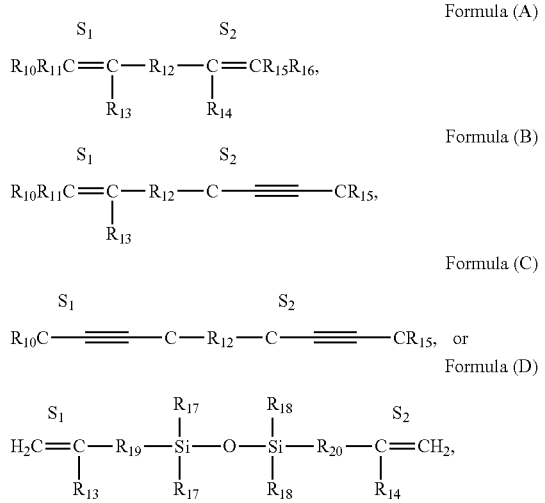

Formula (A)

Formula (B)

Formula (C)

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;

wherein $L_1$-$L_2$ bonds with G through unsaturated sites $S_1$ and $S_2$, wherein the silyl hydride is $Q_uT_vT_p{}^H D_w D_x{}^H M_y{}^H M_z$, wherein Q is $SiO_{4/2}$, T is R' $SiO_{3/2}$, $T^H$ is $HSiO_{3/2}$, D is R'$_2SiO_{2/2}$, $D^H$ is R' $HSiO_{2/2}$, $M^H$ is $H_gR'_{3-g}SiO_{1/2}$, M is R'$_3SiO_{1/2}$, each occurrence of R' is independently C1-C18 alkyl, C1-C18 substituted alkyl, wherein R' optionally contains at least one heteroatom, g has a value of from 0 to 3, each of p, u, v, y and z is independently from 0 to 20, w and x are independently from 0 to 1000, provided that p +x +y equals 1 to 3000, and the valences of the all the elements in the silyl hydride are satisfied;

wherein the compound containing an unsaturated group is selected from the group consisting of an alkyne, a C2-C18 olefin, an unsaturated aryl ether, a vinyl-functional silane, and combinations thereof.

14. The process of claim 13 comprising the step of removing the complex from the hydrosilylation product by magnetic separation and/or filtration.

15. The process of claim 13 wherein in connection with Formula (I), each of $L_1$ and $L_2$ is independently —$CH_2SiR^{60}{}_3$, each occurrence of $R^{60}$ is C1-C18 alkyl, C1-C18 substituted alkyl, aryl or substituted aryl.

16. A process for the hydrosilylation of a composition containing a silyl hydride and a compound containing at least one unsaturated group, the process comprising: (i) contacting the composition with a complex according to Formula (I), optionally in the presence of a solvent, to cause the silyl hydride to react with the compound containing at least one unsaturated group to produce a hydrosilylation product containing said complex, and (ii) optionally removing the complex from the hydrosilylation product, wherein the complex of Formula (I) is

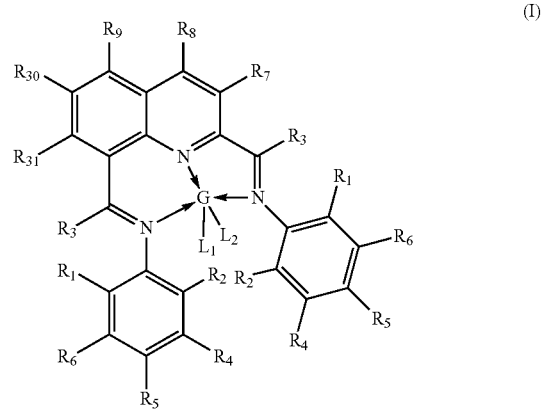

(I)

wherein:

G is Mn, Fe, Ni, or Co;

each occurrence of $R_1$, $R_2$, $R_3$, $R_4$, $R_5$, $R_6$, $R_7$, $R_8$, $R_9$, $R_{30}$ and $R_{31}$ is independently hydrogen, an inert functional group, C1-C18 alkyl, C1-C18 substituted alkyl, aryl, or substituted aryl, wherein optionally each of $R_1$ to $R_9$, $R_{30}$ and $R_{31}$ may independently contain at least one heteroatom;

optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;

$L_1$ and $L_2$ each is a C1-C18 alkyl, C1-C18 substituted alkyl, aryl, substituted aryl, C2-C18 alkenyl or C2-C18 alkynyl, or $L_1$-$L_2$ together is one of the following:

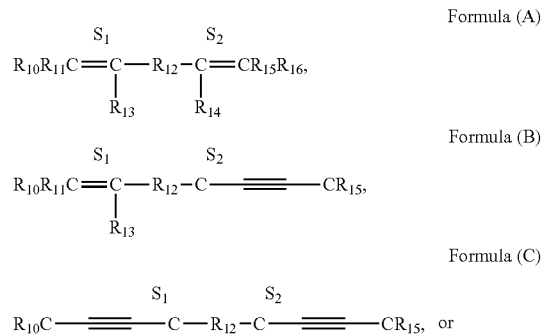

Formula (A)

Formula (B)

Formula (C)

-continued

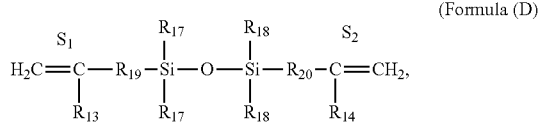

(Formula (D))

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;

wherein $L_1$-$L_2$ bonds with G through unsaturated sites $S_1$ and $S_2$, wherein the silyl hydride is selected from the group consisting of $R_aSiH_{4-a}$, $(RO)_aSiH_{4-a}$, $HSiR_a(OR)_{3-a}$, and combinations thereof, wherein each occurrence of R is independently C1-C18 alkyl, C1-C18 substituted alkyl, ary, or substituted aryl, wherein R optionally contains at least one heteroatom, each occurrence of a independently has a value of from 1 to 3;

wherein the compound containing an unsaturated group is selected from the group consisting of an alkyl-capped allyl polyether, a vinyl functionalized alkyl-capped allyl or methallyl polyether, an alkyne, an unsaturated cycloalkyl epoxide, a terminally unsaturated acrylate or methyl acrylate, an unsaturated aryl ether, an unsaturated aromatic hydrocarbon, an unsaturated cycloalkane, a vinyl-functionalized polymer, a vinyl-functionalized silane, a vinyl-functionalized silicone, and combinations thereof.

17. The process of claim 16 comprising the step of removing the complex from the hydrosilylation product by magnetic separation and/or filtration.

18. A process for the hydrosilylation of a composition containing a silyl hydride and a compound containing at least one unsaturated group comprising (i) providing a complex according to Formula (II); (ii) contacting the complex, optionally in the presence of a solvent, with an activator shortly before, simultaneously or after contacting the complex with the composition, to cause the silyl hydride to react with the compound containing at least one unsaturated group to produce a hydrosilylation product containing said complex and/or derivatives thereof, and (iii) optionally removing the complex and/or derivatives thereof from the hydrosilylation product wherein the complex of formula (II) is

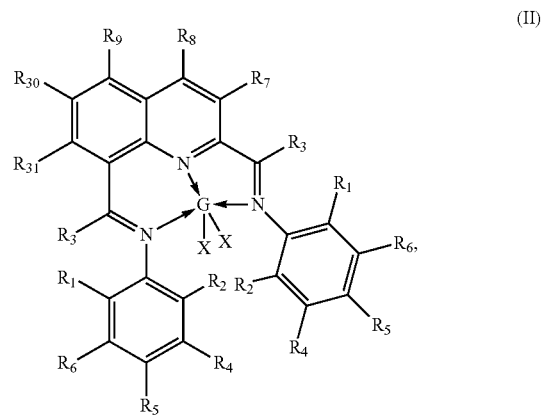

(II)

wherein:

G is Mn, Fe, Ni, or Co;

each occurrence of $R_1$, $R_2$, $R_3$, $R_4$, $R_5$, $R_6$, $R_7$, $R_8$, $R_9$, $R_{30}$ and $R_{31}$ is independently hydrogen, an inert functional group, C1-C18 alkyl, C1-C18 substituted alkyl, aryl, or substituted aryl, wherein optionally each of $R_1$ to $R_9$, $R_{30}$ and $R_{31}$ may independently contain at least one heteroatom;

optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;

wherein X is an anion;

wherein the silyl hydride is $Q_uT_vT_p^HD_wD^H_xM^H_yM_z$, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $H_gR'_{3-g}SiO_{1/2}$, M is $R'_3SiO_{1/2}$, each occurrence of R' is independently C1-C18 alkyl, C1-C18 substituted alkyl, wherein R' optionally contains at least one heteroatom, g has a value of from 0 to 3, each of p, u, v, y and z is independently from 0 to 20, w and x are independently from 0 to 1000, provided that p+x+y equals 1 to 3000, and the valences of the all the elements in the silyl hydride are satisfied, wherein the compound containing an unsaturated group is selected from an alkyne, a C2-C18 olefin, an unsaturated aryl ether, a vinyl-functional silane, and combinations thereof.

19. The process of claim 18 wherein the activator is a reducing agent having a reduction potential more negative than –0.6 v versus ferrocene.

20. The process of claim 18 wherein the activator is selected from sodium naphthalenide, Mg(butadiene) ●2THF, NaEt$_3$BH, Mg(Anthracenide) ●3THF, diisobutylaluminium hydride, and combinations thereof.

21. A process for the hydrosilylation of a composition containing a silyl hydride and a compound containing at least one unsaturated group comprising (i) providing a complex according to Formula (II); (ii) contacting the complex, optionally in the presence of a solvent, with an activator shortly before, simultaneously or after contacting the complex with the composition, to cause the silyl hydride to react with the compound containing at least one unsaturated group to produce a hydrosilylation product containing said complex and/or derivatives thereof, and (iii) optionally removing the complex and/or derivatives thereof from the hydrosilylation product wherein the complex of formula (II) is

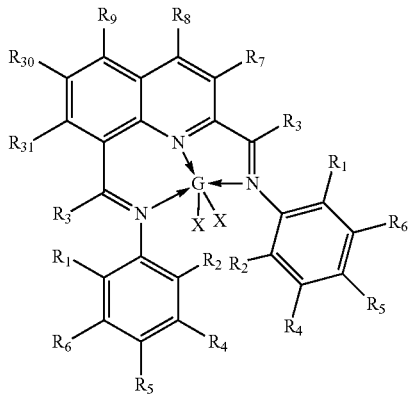

wherein:
  G is Mn, Fe, Ni, or Co;
  each occurrence of $R_1$, $R_2$, $R_3$, $R_4$, $R_5$, $R_6$, $R_7$, $R_8$, $R_9$, $R_{30}$ and $R_{31}$ is independently hydrogen, an inert functional group, C1-C18 alkyl, C1-C18 substituted alkyl, aryl, or substituted aryl, wherein optionally each of $R_1$ to $R_9$, $R_{30}$ and $R_{31}$ may independently contain at least one heteroatom;
  optionally any two of $R_3$, $R_7$, $R_8$, $R_9$, $R_{30}$, and $R_{31}$ vicinal to one another taken together may form a ring being a substituted or unsubstituted, saturated, or unsaturated cyclic structure;
  wherein X is an anion;
  wherein the silyl hydride is selected from the group consisting of $R_aSiH_{4-a}$, $(RO)_aSiH_{4-a}$, $HSiR_a(OR)_{3-a}$, and combinations thereof, wherein each occurrence of R is independently C1-C18 alkyl, C1-C18 substituted alkyl, aryl, substituted aryl, wherein R optionally contains at least one heteroatom, each occurrence of a independently has a value of from 1 to 3,
  wherein the compound containing an unsaturated group is selected from the group consisting of an alkyl-capped allyl polyether, a vinyl functionalized alkyl-capped allyl or methallyl polyether, an alkyne, an unsaturated cycloalkyl epoxide, a terminally unsaturated acrylate or methyl acrylate, an unsaturated aryl ether, an unsaturated aromatic hydrocarbon, an unsaturated cycloalkane, a vinyl-functionalized polymer, a vinyl-functionalized silane, a vinyl-functionalized silicone, and combinations thereof.

22. The process of claim 16, wherein the compound containing an unsaturated group is a polyoxyalkylene having the generic formula:

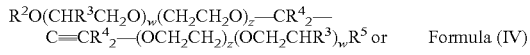

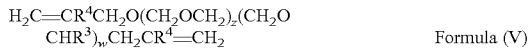

wherein each occurrence of $R^1$ is an unsaturated organic group containing from 2 to 10 carbon atoms, each occurrence of $R^2$ is independently vinyl, or a polyether capping group of from 1 to 8 carbon atoms, each occurrence of $R^3$ and $R^4$ are independently monovalent hydrocarbon groups, each occurrence of z is 0 to 100 inclusive, each occurrence of $R^5$ is independently hydrogen, vinyl, or a polyether capping group of from 1 to 8 carbon atoms, and each occurrence of w is 0 to 100 inclusive.

23. The process of claim 21, wherein the compound containing an unsaturated group is a polyoxyalkylene having the generic formula:

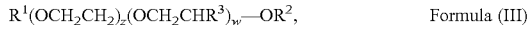

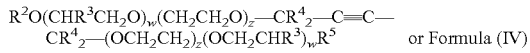

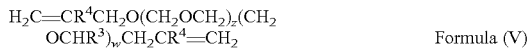

wherein each occurrence of $R^1$ is an unsaturated organic group containing from 2 to 10 carbon atoms, each occurrence of $R^2$ is independently vinyl, or a polyether capping group of from 1 to 8 carbon atoms, each occurrence of $R^3$ and $R^4$ are independently monovalent hydrocarbon groups, each occurrence of z is 0 to 100 inclusive, each occurrence of $R^5$ is independently hydrogen, vinyl, or a polyether capping group of from 1 to 8 carbon atoms, and each occurrence of w is 0 to 100 inclusive.

* * * * *